United States Patent [19]

Nilsson et al.

[11] Patent Number: 6,096,552
[45] Date of Patent: Aug. 1, 2000

[54] METHOD FOR DETERMINING THE CONCENTRATION OF COLORED COMPOUNDS IN MEAT JUICE

[75] Inventors: Bertil Nilsson, Bjärred, Sweden; Sven-Erik Nilsson, Borex, Switzerland; Anders Williamsson, Helsingborg, Sweden; Jan Lilja, Gland, Switzerland

[73] Assignee: Migrata U.K. Ltd., Limassol, Cyprus

[21] Appl. No.: 09/204,356

[22] Filed: Dec. 4, 1998

Related U.S. Application Data

[63] Continuation of application No. PCT/SE97/00983, Jun. 5, 1997.

[30] Foreign Application Priority Data

Jun. 5, 1996 [SE] Sweden ................................. 9602237

[51] Int. Cl.⁷ .................................................. G01N 33/12
[52] U.S. Cl. .............................. 436/21; 436/20; 436/165; 436/177; 426/231; 426/233; 422/82.05; 422/82.09; 422/99; 422/100; 422/101; 422/102
[58] Field of Search .............................. 436/20, 165, 21, 436/177; 426/231, 233; 422/82.05, 82.09, 99, 100, 101, 102

[56] References Cited

U.S. PATENT DOCUMENTS

| | | | |
|---|---|---|---|
| 4,088,448 | 5/1978 | Lilja et al. ................................ | 23/259 |
| 4,654,197 | 3/1987 | Lilja et al. ................................ | 422/56 |
| 5,088,822 | 2/1992 | Kanda ..................................... | 356/326 |
| 5,286,454 | 2/1994 | Nilsson et al. ........................... | 422/102 |
| 5,472,671 | 12/1995 | Nilsson et al. ........................... | 422/102 |
| 5,674,457 | 10/1997 | Williamsson et al. ................... | 422/102 |

FOREIGN PATENT DOCUMENTS

0416658A1  3/1991  European Pat. Off. .

OTHER PUBLICATIONS

"Colour Determination of Beef Juices as an Indicator of Beef Cooking Temperatures", A.D. Nusimovich et al., *Meat Science*, vol. 3, No. 3, (1979) pp. 233–244.

"Determination of total haem pigments in meat products" Nihon Chikusan Gakkai–ho, *Japanese Journal of Zootechnical Science*, vol. 50, No. 1 (1979) pp. 15–21 (Dialog Information Services, File 51, FSTA, Accession No. 00175264).

"Determination of Cooked Sausage Quality by Colour— Comprises Analysing the Reflected Light from Sample Surface" G.Z. Yakubov et al. (Dialog Information Services, File 351, WPIL, Accession No. 010732123).

"Methods for Detecting Processing Temperatures of Previously Cooked Meat and Poultry Products—A Review" W.E. Townsend et al., *Journal of Food Protection*, vol. 52, No. 2, (Feb., 1989) pp. 128–135.

*Primary Examiner*—Randy Gulakowski
*Assistant Examiner*—S. Carrillo
*Attorney, Agent, or Firm*—Burns, Doane, Swecker & Mathis, L.L.P.

[57] ABSTRACT

A method is provided for monitoring the cooking temperature of meat patties. More specifically, a method is provided for monitoring the cooking temperature of meat patties by determining the concentration of colored compounds, such as myoglobin, in meat juice.

14 Claims, 1 Drawing Sheet

METHOD FOR DETERMINING THE CONCENTRATION OF COLORED COMPOUNDS IN MEAT JUICE

This is a continuation of International Application No. PCT/SE97/00983, filed Jun. 5,1997, that designates the United States of America and which claims priority from Swedish Application No. 9602237-1, filed Jun. 5, 1996.

BACKGROUND OF THE INVENTION

1. Field of the Invention

The present invention concerns a method of monitoring the cooking temperature of meat patties. More specifically the present invention concerns a method of monitoring-the cooking temperature of meat patties by determining the concentration of coloured compounds in meat juice.

2. Description of the Related Art

In the US, rules for controlling meat have been strengthened since the incident with bacterial contamination of meat was discovered in a Jack in the Box restaurant. Food Safety and Inspection Service (FSIS; equivalent to FDA) has in 1993 sent out directives which should be followed and inspections are carried out by local health units Since 1996 similar directives in Europe prescribe that each food processing company should work in a preventive way. Listeria monocytogenes are the most serious contaminating bacteria but also Salmonella, *E.coli* O157:H7 and Staphylococcus aureus are of interest to monitor in all types of food. Since the first incident on bacterial contamination (Jack in the Box), most fast-food chains like McDonalds, Burger King and Wendy's over-cook their hamburgers for safety reasons.

Different methods to determine if patties have been well cooked have been used. FSIS recommends thermocouple thermometers inserted in the patties to verify that a certain temperature has been reached. In Europe meat samples are generally sent to external labs for bacterial analysis. Both temperature and cooking time are of importance for killing bacteria.

Measurements of correct temperature of cooked patties are difficult mainly due to the heat transfer between parts/spots of the patties during the cooking process. A better indicator of meat temperature would be a testing of a meat juice compound, flowing in the pores of the meat during cooking. Myoglobin and catalase (an enzyme) have been suggested for monitoring meat juice temperature.

Myoglobin is the major pigment responsible for fresh meat colour. In fresh meat, the pigment can exist in three different forms: The reduced form of myoglobin is purplish, the oxygenated form is bright red and the oxidised form is brown. Fresh meat colour is determined by the relative abundance of these three forms. The consumer often associates the natural bright red colour to the freshness of the product, since brown colour of the oxidised pigment results from prolonged storage. Myoglobin is found in the muscle and is very similar in structure to haemoglobin. The difference in structure is the number of polypeptide chains. It is fairly insensitive to a change in pH. This is not a major problem with meat since the pH is fairly constant (pH 5.3–5.5). It denatures at temperatures above 150° F. (65.5° C.) and might thus be of interest as a temperature indicator in processing of bovine meat (hamburgers).

One method for checking that meat has been heated to a temperature of about 80° C. is disclosed in an article "Colour Determination of beef juices as an indication of beef cooking temperatures" by Nusimovich, A. D. et al in Meat Science 1979 3(3) 233–244. This method is based on the measurement of the optical density at 10 nm intervals over the wave length range 380–770 nm. It is obvious that this method is comparatively labour-intensive and therefore inadequate for industrial application. Additionally, this method is suggested for checking that a specific virus, the so called foot-and-mouth virus has been eliminated. It is furthermore stated that in this known method the error of prediction is unacceptable large.

OBJECTS AND SUMMARY OF THE INVENTION

An object of the present invention is to provide an industrially applicable method, wherein the error in the indirect end-point temperature measurement is negligible and amount of manual work is minimized.

In brief, the method according to the present invention provides a check for thorough cooking which is based on a measurement of myoglobin optionally in combination with other coloured compounds, such as hemoglobin, by filter photometry.

The method includes the following steps:
a) subjecting a meat sample to compressing for obtaining a meat juice sample;
b) filtering said meat juice sample for removing substances such as lipids which can interfere with the subsequent measurement;
c) introducing the obtained meat juice sample into a microcuvette, preferably a capillary microcuvette having at least one cavity for receiving the sample, whereby the cavity is coated with a modifying additive for keeping the sample in a homogenous solution and for facilitating the introduction of the sample into the cuvette, and
d) performing at least two absorption measurements directly on the sample at at least two predetermined wavelengths, whereby one measurement is a compensation measurement.

BRIEF DESCRIPTION OF THE DRAWINGS

The FIGURE illustrates a microcuvette according to the prior art.

The capillary microcuvette used for the measurement may be of the type generally described in the U.S. Pat. No. 4,088,448. According to the FIGURE, this microcuvette comprises a body member 10 including two planar surfaces defining an optical path and placed at a predetermined distance e.g. at least 0.8 and preferably at least 0.7 mm from one another to determine the optical pathlength and to define at least one cavity 11 having an inlet communicating the at least one cavity with the exterior of the body member, the predetermined di-stance being effective to permit the sample to enter the cavity by capillary force. Most preferably, the cuvette is of the type disclosed in our copending application PCT/SE96/00504, which is hereby incorporated by reference. In brief, the cuvette according to the PCT-application comprises a body member and a cavity including a measuring zone within the body member, whereby the cavity is defined by two opposite, substantially parallel inner surfaces of the body member. The cavity is also defined by an outer peripheral edge including a sample inlet and an inner peripheral zone having a channel of higher capillary force than the measuring zone, whereby both ends of the channel communicate with the exterior of the microcuvette.

Figure 1:
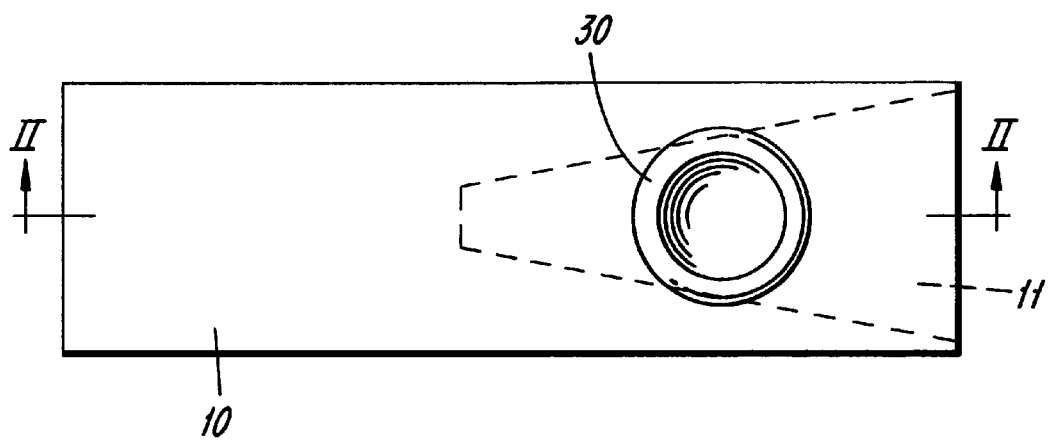

The cuvette disclosed in the U.S. Pat. No. 4,088,448 is intended and used for blood analysis, whereas according to the present invention the sample consists of meat juice and it is a critical feature of the invention that the cavity of the microcuvette is coated with a special modifying additive. The purpose of this additive is to keep the sample in a homogenous solution and to facilitate the introduction of the sample into the cavity. This agent could be a detergent selected from anionic agents such as caprylic acid, lauryl sulphate etc., cationic compounds such as cetyl pyridinium chloride, zwitter ions, such as N-alkyl-N,N-dimethylammonium-1-propane sulphonate (CHAPS) and non-ionic agents, such as N-dodecyl-$\beta$-glucopyranoside. A preferred group of compounds is polyoxyethylene ethers, such as BRIJ52, BRIJ72 and BRIJ 92. Other preferred types are polyoxyethylene derivatives (stearate ethers) such as MYRJ.

Another important feature of the invention is that an absorption measurement is carried out in order to eliminate the effect of optional turbidity in the sample and scratches on the cuvette walls. This compensation measurement is preferably carries out at 880 nm.

According to an alternative embodiment the meat juice sample is introduced into a conventional non-capillary microcuvette having a distance between the cuvette walls less than about 5 mm The invention is further illustrated by the following, non-limiting examples.

Cooking procedure

Frozen hamburgers (brand name Mulberry patties) were used, in which a hole was drilled for continuously measuring internal meat core temperature with a thermocouple. The hamburgers were cooked in a vertical oven. The cooking was stopped at pre-set temperatures.

Sample preparation

Cylindrical pieces of meat were cut out. The pieces were pressed and the meat juice obtained was filtered through a cellulose filter. Samples of juice were drawn for myoglobin determination. Samples were also taken from the top and bottom from the thermocouple locus to see if myoglobin concentration varied. A colour scale on juice and meat (Kansas State University) was used to grade the cooking.

Preparation of microcuvette

Microcuvettes of the type described in the PCT/SE96/00504 were filled with a detergent BRIJ 56 solution and freeze-dried.

Measuring procedure

By capillary action a few ml of each sample was drawn into each microcuvette and the absorbance was measured by filter photometry at 570 nm with a compensation for turbidity at 880 nm. A HemoCue Hemoglobin Photometer available from HemoCue AB, Sweden was used.
The following data were obtained on replicate experiments with meat juice from quaterpounder hamburgers:

| Temperature (° F.) | Temperature (° C.) | Myoglobin (g/l) at TC |
| --- | --- | --- |
| 133.2 | 56.22 | 5.0 |
| 133.2 | 56.22 | 4.9 |
| 140.6 | 60.33 | 5.0 |
| 140.6 | 60.33 | 4.5 |
| 150.6 | 65.89 | 4.1 |
| 150.6 | 65.89 | 3.5 |
| 158.8 | 70.44 | 1.3 |
| 158.8 | 70.44 | 1.3 |
| 170.6 | 77.00 | 1.6 |
| 170.6 | 77.00 | 1.5 |
| 174.9 | 79.39 | 1.2 |
| 174.9 | 79.39 | 1.2 |

Data from three studies at different occasions showed good reproducibility between meat core temperature measured with a thermocouple and the myoglobin concentration. There is a drop in the myoglobin concentration between 65–70° C. (statistically significant; $p<0.001$). This decrease in concentration might be due to a denaturation (or decomposition) of myoglobin. A couple of experiments on meat juice from McDonalds hamburgers gave myoglobin values around zero, which was interpreted as an extensive cooking time of those hamburgers.

Tests have also been performed on imported beef, requiring a temperature of about 80° C. according to FSIS. The decay in the myoglobin concentration can be seen in the following table

| Temperature (° C.) | 76 | 78 | 80 | 82 | 84 |
| --- | --- | --- | --- | --- | --- |
| Experiment 1 (myoglobin g/l) | 1.6 | 0.7 | 0.3 | 0.2 | 0.1 |
| Experiment 2 (myoglobin g/l) | 1.1 | 0.7 | 0.4 | 0.2 | 0.1 |

It can also be concluded that the precision is good and that myoglobin can be used as indicator for mean temperature.

We claim:

1. A method for determining the concentration of colored compounds in meat juice, comprising the steps of filtering a sample of meat juice, introducing the sample in a capillary microcuvette having at least one cavity for receiving the sample, wherein the cavity is coated with a modifying additive for keeping the sample in a homogenous solution and for facilitating the introduction of the sample into the microcuvette; performing at least two absorption measurements by at least two predetermined wavelengths directly on the sample in the microcuvette, wherein one measurement is a compensation measurement, and determining the concentration of colored compounds in the meat juice from said at least two absorption measurements.

2. The method according to claim 1 wherein the compensation measurement is carried out at 880 nm.

3. The method according to claim 1 wherein the modifying additive is a detergent.

4. The method according to claim 1, wherein the colored compounds are selected from the group consisting of myoglobin and hemoglobin.

5. The method according to claim 2 wherein the modifying additive is a detergent.

6. The method according to claim 3 wherein the detergent is selected from the group consisting of caprylic acid, lauryl sulphate, cetyl pyridinium chloride, zwitter ions, and non-ionic agents.

7. The method according to claim 3 wherein the detergent is a polyoxyethylene ether.

8. The method according to claim 3 wherein the detergent is N-alkyl-N,N-dimethylammonium-1-propane sulphonate.

9. The method according to claim 3 wherein the detergent is N-dodecyl-$\beta$-glucopyranoside.

10. The method according to claim 9 wherein the detergent is selected from the group consisting of caprylic acid, lauryl sulphate, cetyl pyridinium chloride, zwitter ions, and non-ionic agents.

11. The method according to claim 9 wherein the detergent is a polyoxyethylene ether.

12. The method according to claim 5 wherein the detergent is N-alkyl-N,N-dimethylammonium-1-propane sulphonate.

13. The method according to claim 5 wherein the detergent is N-dodecyl-β-glucopyranoside.

14. A method for checking thorough cooking of meat patties comprising the steps of
   a) subjecting a meat patty to compression for obtaining a meat juice sample
   b) filtering said meat juice sample
   c) introducing the obtained meat juice sample into a capillary microcuvette having an interior and an exterior, said microcuvette including two planar surfaces placed at a predetermined distance from one another to define an optical pathlength and said planar surfaces defining at least one cavity in the microcuvette, said at least one cavity including a modifying additive for keeping the sample in a homogenous solution and for facilitating the introduction of the sample into the at least one cavity; and having an inlet communicating the at least one cavity with the exterior of the microcuvette, the predetermined distance being effective to permit the sample to enter the cavity by capillary force;
   d) measuring the absorption at at least two predetermined wavelengths directly on the sample wherein one measurement is a compensation measurement;
   e) determining the concentration of colored compounds in the meat juice sample from said at least two absorption measurements; and
   f) determining whether the meat patty has been thoroughly cooked from the concentration of colored compounds in the meat juice sample.

* * * * *